US006849084B2

(12) United States Patent
Rabkin et al.

(10) Patent No.: US 6,849,084 B2
(45) Date of Patent: Feb. 1, 2005

(54) STENT DELIVERY SYSTEM

(75) Inventors: Dmitry Rabkin, Framingham, MA (US); Eyal Morag, East Hampton, MA (US); Yoram Hadar, Netanya (IL); Ophir Perelson, Beverly Hills, CA (US)

(73) Assignee: InTek Technology L.L.C., Wilmington, DE (US)

( * ) Notice: Subject to any disclaimer, the term of this patent is extended or adjusted under 35 U.S.C. 154(b) by 0 days.

(21) Appl. No.: 10/334,402

(22) Filed: Dec. 31, 2002

(65) Prior Publication Data

US 2004/0127912 A1 Jul. 1, 2004

(51) Int. Cl.[7] .................................................. A61F 2/06
(52) U.S. Cl. ...................... 623/1.12; 606/108
(58) Field of Search ............................. 623/1.11, 1.12, 623/1.23; 606/108

(56) References Cited

U.S. PATENT DOCUMENTS

| | | | | |
|---|---|---|---|---|
| 5,064,435 A | * | 11/1991 | Porter | 623/23.7 |
| 5,201,757 A | * | 4/1993 | Heyn et al. | 606/198 |
| 5,354,308 A | * | 10/1994 | Simon et al. | 623/1.15 |
| 5,415,664 A | * | 5/1995 | Pinchuk | 623/1.11 |
| 5,690,644 A | * | 11/1997 | Yurek et al. | 623/1.11 |
| 5,807,404 A | * | 9/1998 | Richter | 623/1.16 |
| 5,836,966 A | * | 11/1998 | St. Germain | 606/198 |
| 5,906,619 A | * | 5/1999 | Olson et al. | 606/108 |
| 5,938,697 A | * | 8/1999 | Killion et al. | 623/1.15 |
| 5,989,280 A | * | 11/1999 | Euteneuer et al. | 623/1.1 |
| 6,030,413 A | * | 2/2000 | Lazarus | 623/1.11 |
| 6,063,112 A | * | 5/2000 | Sgro | 623/1.12 |
| 6,066,168 A | * | 5/2000 | Lau et al. | 623/1.16 |
| 6,106,548 A | * | 8/2000 | Roubin et al. | 623/1.15 |
| 6,146,403 A | * | 11/2000 | St. Germain | 623/1.15 |
| 6,159,238 A | * | 12/2000 | Killion et al. | 623/1.11 |
| 6,187,034 B1 | * | 2/2001 | Frantzen | 623/1.11 |
| 6,203,550 B1 | * | 3/2001 | Olson | 606/108 |
| 6,224,609 B1 | * | 5/2001 | Ressemann et al. | 606/108 |
| 6,231,598 B1 | * | 5/2001 | Berry et al. | 623/1.15 |
| 6,325,825 B1 | * | 12/2001 | Kula et al. | 623/1.3 |
| 6,348,065 B1 | * | 2/2002 | Brown et al. | 623/1.16 |
| 6,355,057 B1 | * | 3/2002 | DeMarais et al. | 623/1.15 |
| 6,355,059 B1 | * | 3/2002 | Richter et al. | 623/1.17 |
| 2002/0111666 A1 | * | 8/2002 | Hart et al. | 623/1.11 |
| 2002/0165554 A1 | * | 11/2002 | Dworschak et al. | 606/108 |
| 2003/0163189 A1 | * | 8/2003 | Thompson et al. | 623/1.11 |

* cited by examiner

Primary Examiner—Corrine McDermott
Assistant Examiner—Thomas J Sweet
(74) Attorney, Agent, or Firm—Steinberg & Raskin, P.C.

(57) ABSTRACT

A first stent delivery system provided with a sheath for covering the stent, the sheath including proximal sheath portion adapted to be movable in a proximal direction and a distal sheath portion adapted to be moveable in a distal direction. A second stent delivery system including an outer and intermediate tubular members covering a chamber with a preloaded stent, the outer tubular member being retractable prior to the retraction of the intermediate sheath and release of the stent. A third stent delivery system including with an inflatable balloon at a distal end of the system for fixing the system in place within the vessel prior to the release of the stent thereby insure accurate stent deployment.

29 Claims, 13 Drawing Sheets

STENT DELIVERY SYSTEM

FIELD OF THE INVENTION

This invention relates generally to medical devices, and more particularly to a system for delivering stents of the self-expanding type to a desired location in a vessel to be treated.

BACKGROUND OF THE INVENTION

A stent is a generally longitudinal cylindrical device formed of biocompatible material, such as metal or plastic, which is used in the treatment of stenosis, strictures, or aneurysms in body blood vessels and other tubular body structures, such as the esophagus, bile ducts, urinary tract, intestines or the tracheo-bronchial tree.

A stent is held in a reduced diameter unexpanded configuration within a low profile catheter until delivered to the desired location in the tubular structure, most commonly a blood vessel, whereupon the stent radially expands to an expanded diameter configuration in the larger diameter vessel to hold the vessel open. Radial expansion may be accomplished by manually inflating a balloon which is attached to a catheter in a balloon expanding stent, or the stent may be of the self-expanding type that will radially expand spontaneously once released from the end portion of the delivery catheter.

Generally, self-expanding stents are made from materials that exhibit superelastic properties above a particular transitional temperature, that is, the material rapidly expands once the material is heated above the transitional temperature. For example, most of the currently available self-expanding stents are made from Nitinol which has a transitional temperature from the martensite to austenite state around 20° C. Thus, once a Nitinol stent reaches a temperature of 20° C. the stent will begin to rapidly expand in the radial direction. During the delivery of such stents within the vessel to be treated, the stent reaches the transitional temperature almost as soon as the stent is introduced into the body, i.e. well before the stent is actually released into the vessel and comes into contact with the bloodstream. Accordingly, the stent is maintained in a compressed state within the delivery catheter until the stent is positioned within the desired delivery location. When the stent is released into the vessel, since it has already reached its transitional temperature, and is in a compressed state, it will expand almost instantaneously to its maximum radial diameter.

The present invention relates to self-expanding stents, examples of self-expanding stent designs are shown in U.S. Pat. No. 5,064,435 to Porter; U.S. Pat. No. 5,354,308 to Simon; U.S. Pat. No. 5,569,295 to Lam; U.S. Pat. No. 5,716,393 to Lindenberg; U.S. Pat. No. 5,746,765 to Kleshinski; U.S. Pat. No. 5,807,404 to Richter et al; U.S. Pat. No. 5,836,966 to St. Germain; U.S. Pat. No. 5,938,697 to Killion; U.S. Pat. No. 6,146,403 to St. Germain; U.S. Pat. No. 6,159,238 to Killion; U.S. Pat. No. 6,187,034 to Frantzen; U.S. Pat. No. 6,231,598 to Berry et al.; U.S. Pat. No. 6,106,548 to Roubin et al.; U.S. Pat. No. 6,066,168 to Lau et al.; U.S. Pat. No. 6,325,825 to Kula et al.; U.S. Pat. No. 6,348,065 to Brown et al.; U.S. Pat. No. 6,355,057 to DeMarais et al and U.S. Pat. No. 6,355,059 to Richter et al.

Typically, a self-expanding stent is introduced into a vessel to be treated via a catheter delivery system which contains the compressed stent. The compressed stent is contained within a closed space or chamber at the distal end of the catheter delivery system, the chamber being defined between an inner core member and retractable sheath or sleeve. The retractable sheath functions to maintain the stent in the compressed state until the stent is positioned in its desired location. The catheter delivery system is provided with a lumen through which a guidewire is passed to enable the positioning of the stent containing chamber to the treatment site within the vessel. Once the stent is positioned in the desired treatment site within the vessel, the retractable sheath is retracted in a proximal direction to expose the stent, which expands almost instantaneously to its final diameter as the sheath is being withdrawn. The stent is deployed into the vessel when the sleeve is completely retracted. Delivery systems of this type are described in U.S. Pat. Nos. 6,391,050; 6,375,676; and 5,77,669 which are each discussed in greater detail below.

U.S. Pat. No. 6,391,050 discloses a self-expanding stent delivery system which includes a catheter having an outer tube, the outer tube containing a channel for a guidewire lumen containing a guidewire arranged therein and a pullwire lumen containing a pullwire arranged therein. A distal end of the outer tube is affixed to a dual lumen tube which includes an inner lumen and a pullwire lumen, the guidewire lumen being arranged within the inner lumen. The pullwire lumen is provided with an axial slit from which the pullwire exits, the pullwire being coupled to a retractable sheath of a stent. When the pullwire is retracted the sheath is retracted thereby first exposing a distal end of the stent, then a middle area of the stent and finally the proximal end of the stent, thereby enabling the stent to expand.

U.S. Pat. No. 6,375,676 ("the '676 patent) describes a self-expanding stent and associated stent delivery system. The stent deliver system described in the '676 patent includes a delivery catheter including an inner tubular member which extends within an outer tubular member in a coaxial arrangement. The outer tubular member has a proximal end that is attached to a pull back handle that is designed to move axially. The distal end of the outer tubular member is provided with a flexible restraining sheath which is coupled to the outer tubular member, the sheath being adapted to maintain a stent in a collapsed state until the sheath is retracted. The sheath may be retracted, i.e. moved in a proximal direction, to enable the stent to expand by manually grasping the pull back handle. When the sheath is retracted a distal end region of the stent is exposed first, as the sheath continues to be retracted an intermediate region of the stent is exposed and finally a proximal region of the stent is exposed.

U.S. Pat. No. 5,772,669 ("the '669 patent") discloses a stent delivery system for self expanding stents including a catheter having a stent containing portion near a distal end of the system in which a stent is arranged. The stent delivery system further comprises a proximal outer sheath, a retractable distal sheath which surrounds the stent and a pull back wire that is coupled to the retractable distal sheath. When the pull back wire is pulled proximally the distal sheath is retracted, a distal region of the stent is exposed first, then a middle region of the stent and finally the proximal region of the stent, thereby enabling the stent to fully expand.

A problem in stent delivery systems of the type described above results from the common feature that the stent is gradually exposed in relatively slow unidirectional manner from the distal end region of the stent towards proximal end region of the stent as the outer sheath is retracted. This problem with prior art stent delivery systems manifests itself in a number of clinical problems during deployment of the stent. These problems are discussed in greater detail below.

First, the exposed and expanded distal end of the stent may contact the wall of the vessel and serving as an "anchoring edge" for the remaining stent. In its fully expanded state this edge can no longer be moved, since any movement will be associated with irritation and trauma to the vessel wall. The trauma is caused by the metallic stent edges moving against the delicate inner surface of the vessel wall. Therefore, when using most of the currently available stent designs, once the distal end of the stent is fully expanded the stent is essentially locked into a position and further repositioning of the stent becomes impossible.

Another problem encountered in clinical practice, is related to a "spring effect" in which the retraction of the sheath over the self-expanding stent can cause the stent to behave like a spring. That is, as the sheath is removed, the stored energy in the compressed stent is suddenly released essentially causing the stent to move in a distal direction in an unpredictable way. This effect is exaggerated in stents having a short overall length. In such stents, when the distal end is exposed and becomes flared, but has not yet made contact with the vessel wall, and the proximal end of the stent is covered by only a few millimeters of the outer sheath, and then the sleeve is completely retracted, the stent tends to "jump" in a distal direction and will thus likely end up in the wrong final location.

Another difficulty which may be encountered during the release of self-expanding stents when using conventional delivery systems is related to a "push-pull" phenomenon. The "push-pull" phenomenon is encountered most dramatically in long catheter delivery systems, which are placed in tortuous vessels. The "push-pull" phenomenon presents itself as forward motion of the inner core in relation to the retractable sheath at the distal end of the system, as the sheath is being retracted to expose the stent. In practical terms, it may result in a forward motion of the stent during its deployment thereby resulting in the inaccurate positioning of the stent.

The above discussed problems in prior art stent delivery systems make the accurate positioning of self-expanding stents within the desired location difficult.

It is therefore an object of the present invention to provide a new and improved stent delivery system that overcomes the shortcomings of the prior art stent delivery systems.

It is another object of the present invention to provide a new and improved stent delivery system that minimizes stent movement during deployment of the stent thereby enabling the accurate positioning of the stent within the vessel to be treated.

It is yet another object of the present invention to provide a new and improved stent delivery system that prevents/minimizes the spring effect, and jumping of the stent caused by the spring effect, when the stent is deployed.

It is yet another object of the present invention to provide a new and improved stent delivery system that minimizes the "push-pull" phenomenon.

SUMMARY OF THE INTERVENTION

Briefly, these and other objects are attained by providing a stent delivery system comprising a catheter which, according to a first aspect of the invention, has a sheath for covering a collapsed self-expanding stent during delivery, the sheath including a proximal sheath portion adapted to be movable in a controlled manner in a proximal direction, and a distal sheath portion adapted to be moveable in a controlled manner in a distal direction, to expose and release the stent in a controlled manner when the stent has been delivered to the desired region of the vessel to be treated. The proximal sheath portion has a distal edge and the distal sheath portion has a proximal edge, the distal edge of the proximal sheath portion and the proximal edge of the distal sheath portion being arranged in a region situated between the ends of the stent. During delivery, the distal edge of the proximal sheath portion and the proximal edge of the distal sheath portion are in mating engagement with each other so that the entire stent is covered by the sheath portions during delivery.

Upon the stent being located at the desired location in the vessel, the proximal and distal sheath portions are moved apart (i.e. the sheath is opened) by the physician in a controlled manner to expose only a mid-region of the stent, but so that the proximal sheath portion still covers and restrains a proximal end region (including the proximal end) of the stent and so that the distal sheath portion still covers and retrains a distal end region (including the distal end) of the stent. The stent delivery system according to the present invention therefore initially partially opens to expose and permit only a partial and minimal expansion or bulging of a mid-region of the stent. Since only a mid-region of the stent is exposed and released prior to the exposure and release of the end regions (including the ends), the expansion or bulging of the mid-region is controlled so that it does not engage the vessel wall and so that the position of the catheter can be finely adjusted to accurately position the stent at the precise desired location in the vessel. Only when the physician is absolutely satisfied that the stent is accurately positioned in the vessel is the sheath completely opened by moving the proximal and distal sheath portions in the proximal and distal directions respectively until the end regions (including the ends) of the stent are completely exposed and released.

Simultaneous opposite motions of the distal sheath portion in the distal direction and the proximal sheath portion in the proximal direction tend to balance each other thereby preventing undesired forward movement of the tip of the catheter and stent during deployment which can occur with prior art systems, especially when used to introduce stents through tortuous vascular passages. When using prior art delivery systems for self-expanding stents, once the distal portion of the stent is exposed it expands in a flared configuration and the distal end of the stent can touch or come close to the vessel wall. At that stage it is unsafe to try to reposition the stent. In addition, the stent cannot be safely placed back within the sheath once a few millimeters of the stent is exposed, and expands, outside the sheath. When undesired forward motion of the distal end of the catheter occurs in prior art delivery systems the stent must be deployed even if it is not in desired delivery location since further repositioning of the stent is impossible. The present invention avoids this problem since undesired movement of the stent is minimized due to the movement of the proximal and distal sheath portions in opposite directions. Further, since the partially exposed stent is still held at both ends, it can be safely repositioned into the specific desired delivery location prior to its complete deployment.

Finally, since the mid-region of the stent is exposed prior to the exposure and release of the end regions of the stent, the spring effect, and jumping of the stent caused by the spring effect, is eliminated.

According to second aspect of the invention a stent delivery system includes an outer tubular member, an intermediate tubular member arranged within the outer tubular member, an inner tubular member arranged within the intermediate tubular member and a stent arranged between the inner tubular member and the intermediate tubular member. The stent is arranged within the tubular members such that distal ends of each of the tubes extend beyond a distal end of the stent such that the stent is completely covered. Upon reaching the desired position in the vessel, the physician manually and independently retracts the outer and intermediate tubular members in a proximal direction. Specifically, the outer tubular member is first retracted to a clearance position relative to the stent, i.e. a position in which the distal end of the outer tubular member is situated proximally of the proximal end of the stent. Thereafter, the intermediate tubular member is retracted to a similar clearance position relative to the stent to thereby expose and release the stent. Since the outer tubular member is retracted first, before retraction of the intermediate member and the release of the stent, the effect of the "push pull" phenomenon is significantly reduced. Retraction of the outer tubular member removes the "slack" in the catheter system shaft, which can be created during introduction of the system through the tortuous vascular passages. The stent is then deployed by manual retraction of the intermediate tubular member by the operator.

According to a third aspect of the invention a stent delivery system includes an outer tubular member, an inner tubular member, a stent arranged between the inner tubular member and the outer tubular member, and an inflatable balloon coupled to a tip of the catheter, the balloon being distally arranged relative to the stent and to the distal end of the outer tubular member. During stent delivery, the system is initially positioned with the stent situated at the desired treatment site in a conventional manner. The balloon is then inflated via a balloon lumen until the surface of the balloon wall is placed in abutment with the wall of the vessel to effectively lock the delivery system in place in the vessel thereby eliminating the possibility of any undesired movement of the system during stent deployment. After the balloon is inflated, the outer tubular member is retracted to thereby release the stent. Since the system is effectively locked in place by the engagement of the inflated balloon with the vessel wall, inadvertent movement of the system during the deployment of the stent is eliminated and accurate placement of the stent is promoted.

BRIEF DESCRIPTION OF THE DRAWINGS

The present invention and many of its attendant advantages will be more fully understood by reference to the following detailed description when viewed with accompanying drawings in which.

DETAILED DESCRIPTION OF THE INVENTION

Figure 1:
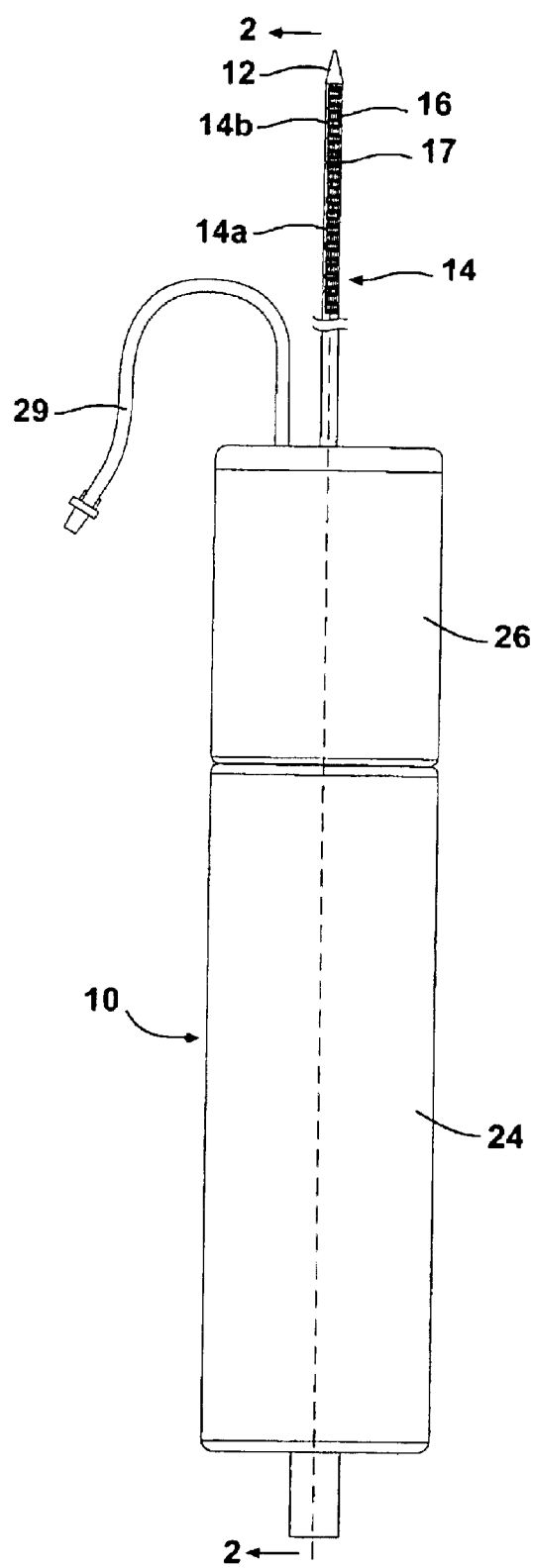
FIG. 1 shows a side elevation view of a stent delivery system according to a first aspect of the invention showing a preloaded stent covered by a sheath having proximal and distal sheath portions at a distal end of the system and a mechanism for controlling the movement of the proximal sheath portion in a proximal direction and the movement of the distal sheath portion in a distal direction.

As shown in FIG. 1, the stent delivery system according to the present invention includes a a sheath assembly 14 for retaining a self-expanding stent 16 at a distal end of the system, the sheath assembly 14 including a proximal sheath portion 14a and a distal sheath portion 14b. The stent delivery system further includes a mechanism 10 for controlling the movement of the proximal sheath portion 14 in a proximal direction and the movement of the distal sheath portion 14b in a distal direction. The proximal sheath portion 14a and the distal sheath portion 14b are operably coupled to the mechanism 10 such that proximal sheath 14a and distal sheath portion 14b can be moved apart by the physician in a controlled manner, by operation of the mechanism 10, to thereby expose and deploy the self expanding stent 16. The details regarding the operative connection between the proximal sheath portion 14a and the mechanism 10, as well as the operative connection between the distal sheath portion 14b and the mechanism 10, are discussed in further detail below.

The proximal sheath portion 14a and the distal sheath portion 14b are distinct members that initially abut one another at location 17 to thereby maintain the stent 16 fully covered in a compressed state. Although the location 17 is shown in the Figures at a location that substantially corresponds to a midpoint along the length of the stent 16 it is possible that the specific point of abutment between the proximal sheath portion 14a and the distal sheath portion 14b may vary somewhat relative to the midpoint of the stent 16. However the location 17 of abutment between the proximal sheath portion 14a and distal sheath portion 14b must be situated somewhere between the termianl ends of the stent 16.

The stent 16 is preferably a nitinol alloy or mesh self-expanding stent. Stents of this type are well known in the art and require no further discussion herein.

As best seen in FIGS. 4a–4d the system according to the present invention further includes an inner tubular member 18. Although the inner tubular member 18 is shown in the drawings as being tubular in nature, it is possible that the inner tubular member 18 could have a solid construction, i.e. not include a central lumen. The inner tubular member 18 can be made of plastic, metal or other suitable material. The inner tubular member 18 is coupled at a proximal end thereof to the mechanism 10 (See FIG. 2a) and at a distal end thereof to the distal tip 12 of catheter. The inner tubular member 18 encloses a guidewire 19 which aids in the navigation of the catheter to and through the vessel to be treated. The inner tubular member 18 can have a single central lumen for the guidewire or it may have a multichannel construction. The inner tubular member 18 is preferably made of a flexible but incompressible construction such as a polymer encapsulated braid or coil, or a thin walled plastic or metallic tube as known in the art.

The construction of the mechanism 10 will now be described with reference to FIGS. 2a–2d and FIG. 3. Mechanism 10 includes a rotatable outer proximal housing 24 and a stationary distal housing 26. As shown, the proximal rotatable housing 24 has a first series of internal threads 28 arranged on an internal surface thereof. The rotatable proximal housing 24 further includes an annular throat portion 30. The annular throat portion 30 includes a series of internal threads 32 arranged on an internal surface of the throat portion 30 as shown. The annular throat portion 30 is adapted to engage an annular sleeve 34 which is provided with a series of threads 36 arranged on an outer surface thereof. The threads 36 of the annular sleeve 34 are adapted to mate with the threads 32 arranged on the internal surface of the throat portion 30.

Mechanism 10 further includes cup shaped insert 38. As best seen FIG. 3, the external surface of the cup shaped insert 38 is provided with a plurality of threads 40. Threads 40 of the cup shaped insert 38 are adapted to mate with the threads 28 provided on the internal surface of the proximal rotatable housing 24 (shown in FIGS. 2a–2d). The external surface of the cup shaped insert 38 is further provided with a plurality of axial channels 42 that are recessed relative to the threads 40. Axial channels 42 are adapted to mate with a plurality of corresponding keys 44 which extend from an internal surface of stationary distal housing 26 as shown in FIGS. 2a–2d. Axial channels 42 and keys 44 cooperate to enable an axial movement of the cup shaped insert 38 relative to the stationary distal housing 26 while at the same time preventing the rotational movement of the cup shaped insert 38. The distal end of the cup shaped insert 38 is fixedly attached to the proximal sheath portion 14a at location 46 so that as the cup shaped insert 38 moves in proximal direction the proximal sheath portion 14a is drawn in a proximal direction.

Mechanism 10 further includes a plunger 48 having a head portion 48a and a axially extending stem portion 48b which extends towards a distal end of the mechanism. Inner tubular member 18 is coupled to the head portion 48a of the plunger 48 and the inner tubular member 18 passes through body of the mechanism as shown. The head portion 48a has a portion that extends outward from the rotatable proximal housing 24. As shown the head portion 48 is provided with a throughbore that enables the guidewire 19 to be fed through the mechanism 10 as shown. Cup shaped insert 38 and stationary distal housing 26 are respectively provided with centrally aligned bores 50 and 52 to permit the passage of the inner tubular member 18 through the mechanism 10. Mechanism 10 is provided with a flushing port 29 for irrigation of the lumen between the sheath 14 and the inner tubular member 18, including the chamber with the preloaded stent 16.

Figure 5A:
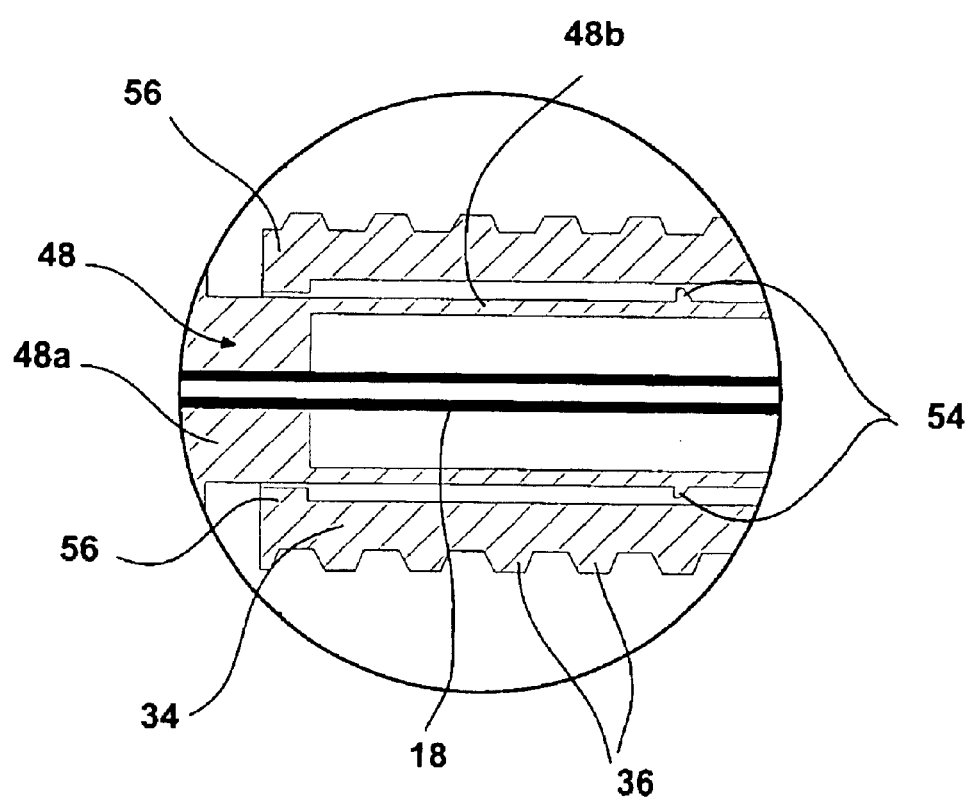
FIG. 5A is an enlarged detail cross sectional view showing the annular sleeve and the stem portion of the plunger of the deployment mechanism in a state in which the annular sleeve is free to move in a distal direction and the stem portion of the plunger remains stationary.
Figure 5B:
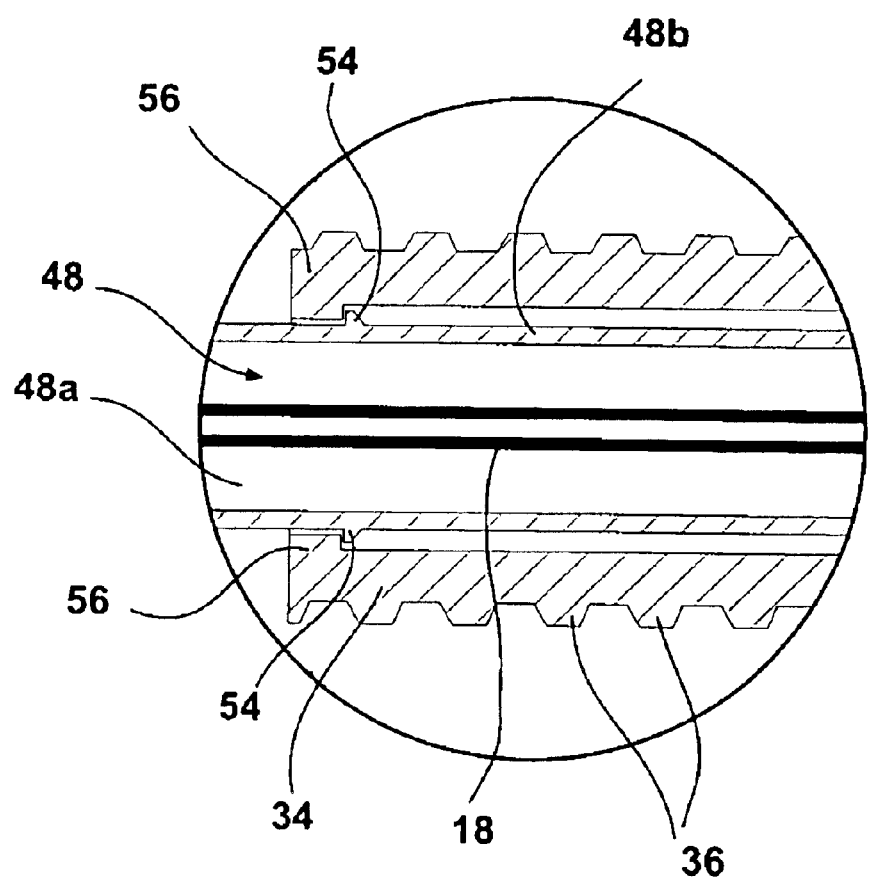
FIG. 5B is an enlarged detail cross section view showing the annular sleeve and the stem portion of the plunger of the deployment mechanism in a state in which the annular sleeve and stem portion are operably coupled such that they move conjointly in the distal direction.

As shown, stem portion 48b of the plunger 48 extends into and is received within the axial bore of annular sleeve 34. As shown in FIGS. 5a and 5b, stem portion 48b of the plunger 48 is provided with a radial outwardly extending lip 54. As will be described in greater detail below with respect to the operation of the delivery system, the lip 54 is structured and arranged so that as annular sleeve 34 moves in a distal direction, a radial inwardly extending lip 56 of the annular sleeve 34 is placed in abutment with the radial outwardly extending lip 54 of the plunger stem portion 48b (see FIG. 5b), such that further distal movement of annular sleeve 34 causes the plunger 48 to move conjointly with annular sleeve 34 in a distal direction.

Figure 2A:
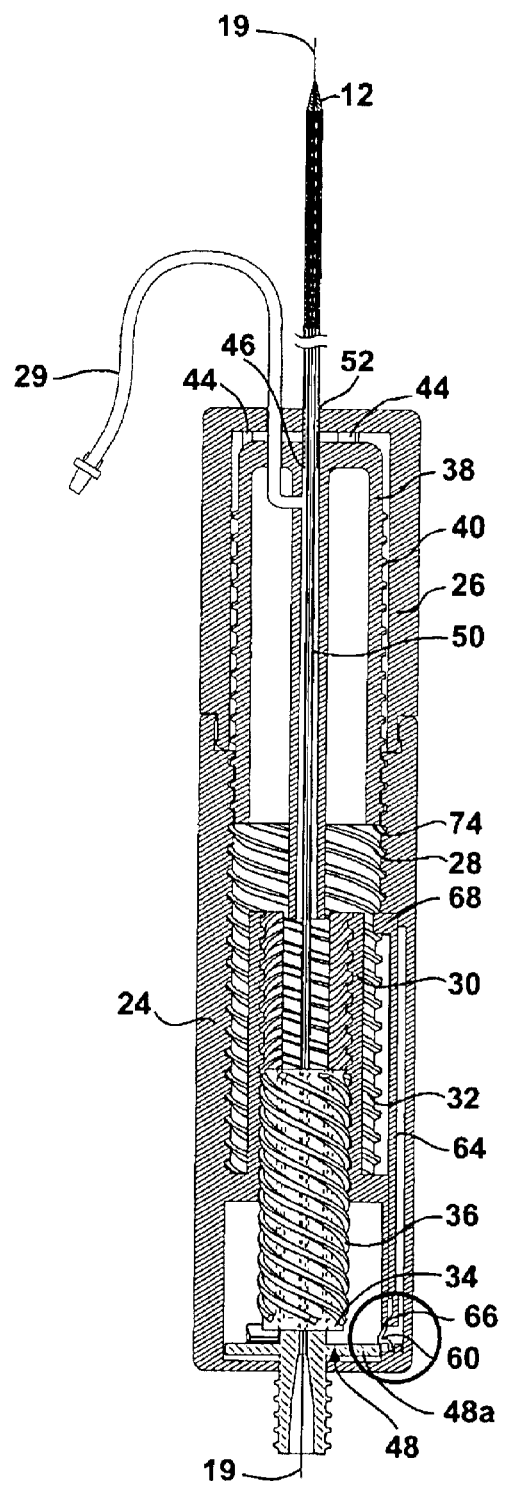
FIGS. 2A–2D are cross section views of the stent delivery system shown in FIG. 1 taken along line 2—2, each of the figures showing the stent in progressive states of expansion and showing the mechanical operation of the deployment mechanism used to deploy the stent.
Figure 2B:
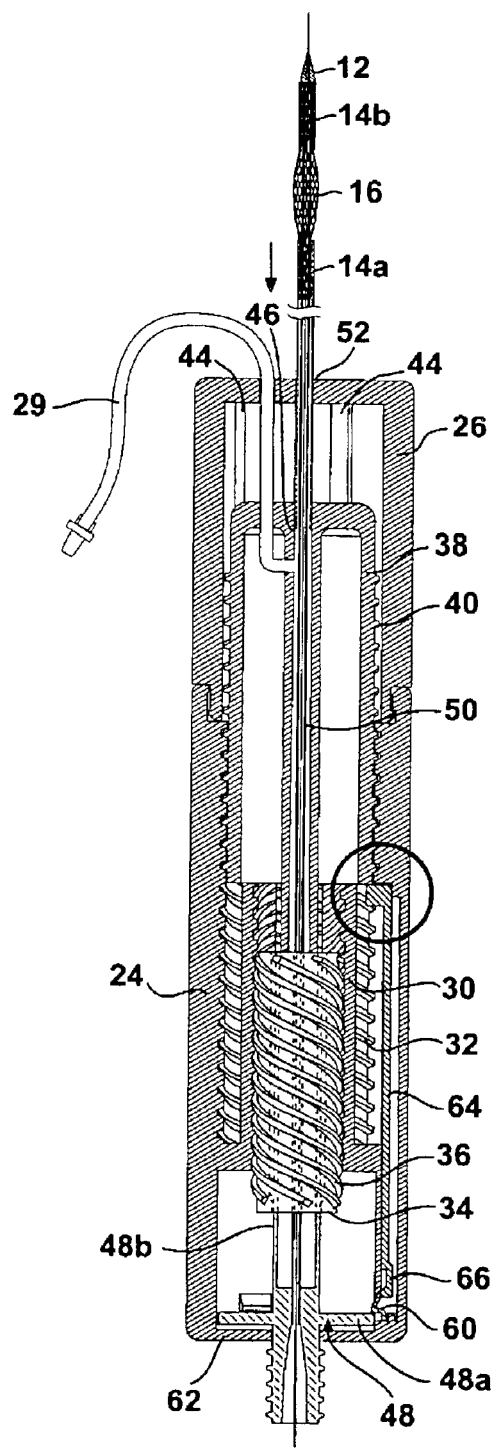
Figure 2C:
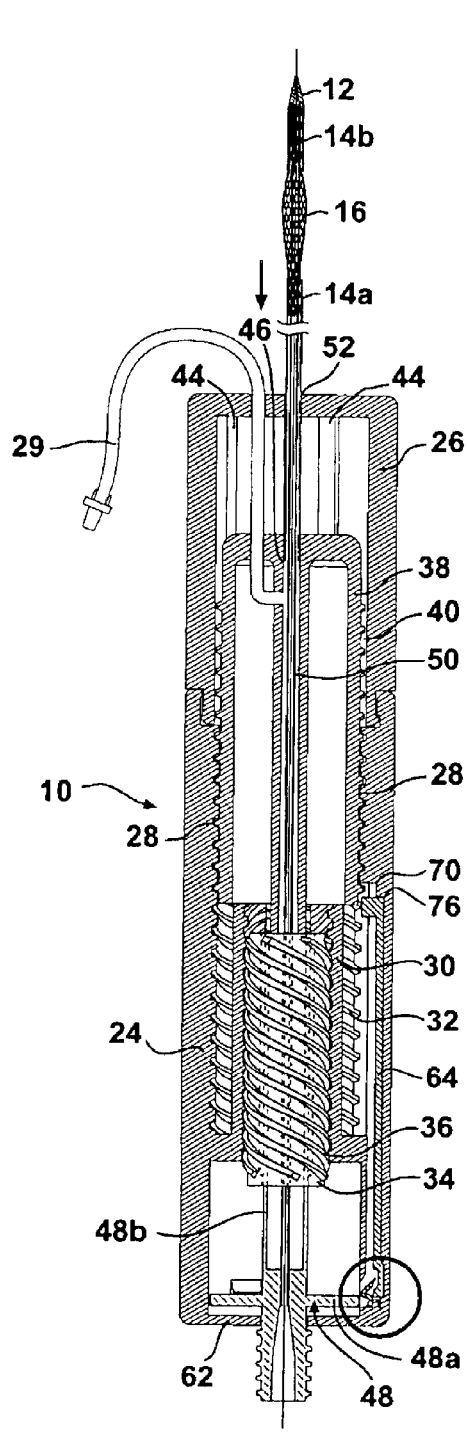
Figure 2D:
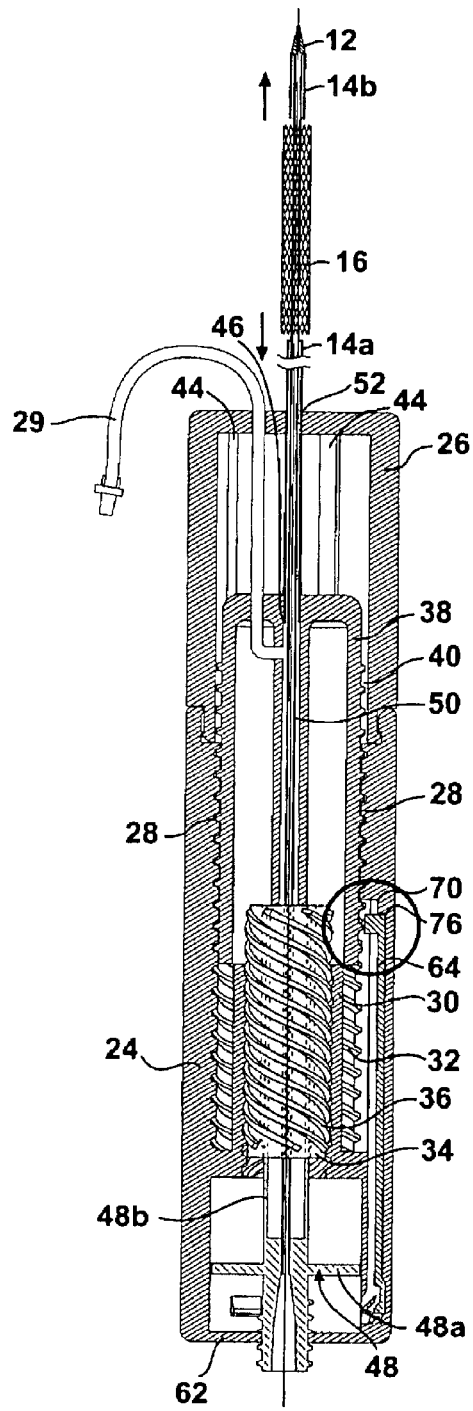
Figure 2E:
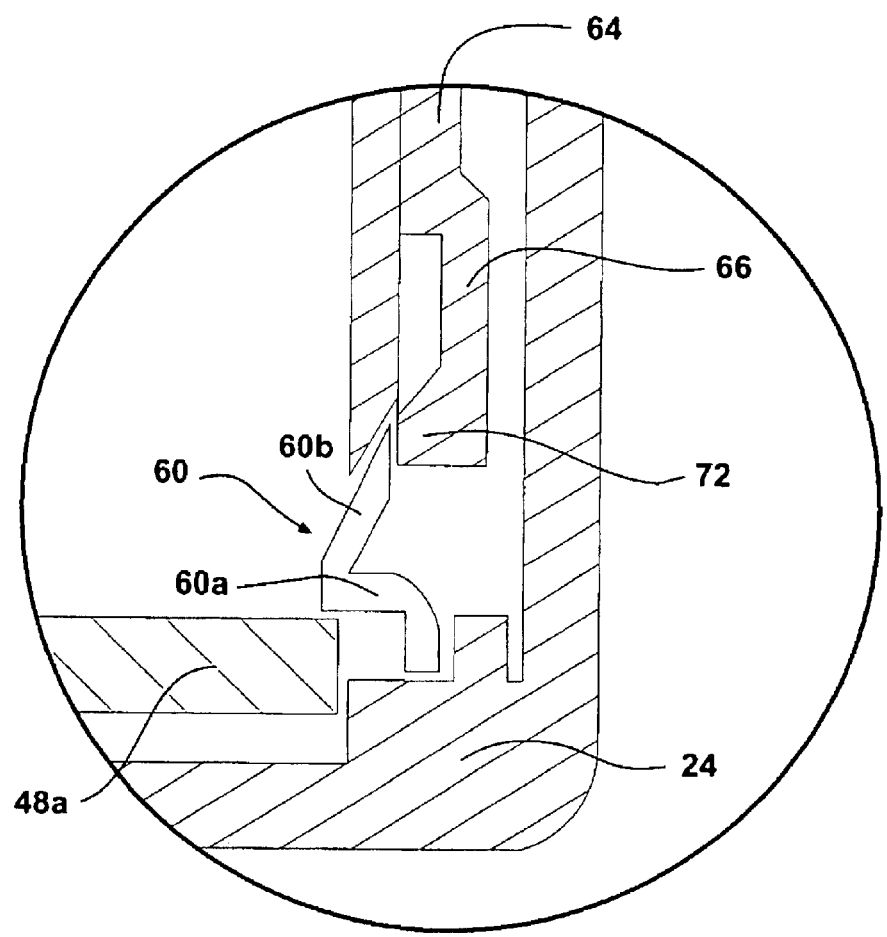
FIG. 2E is a detailed section view of the proximal portion of the hinge mechanism circled in FIG. 2A.
Figure 2F:
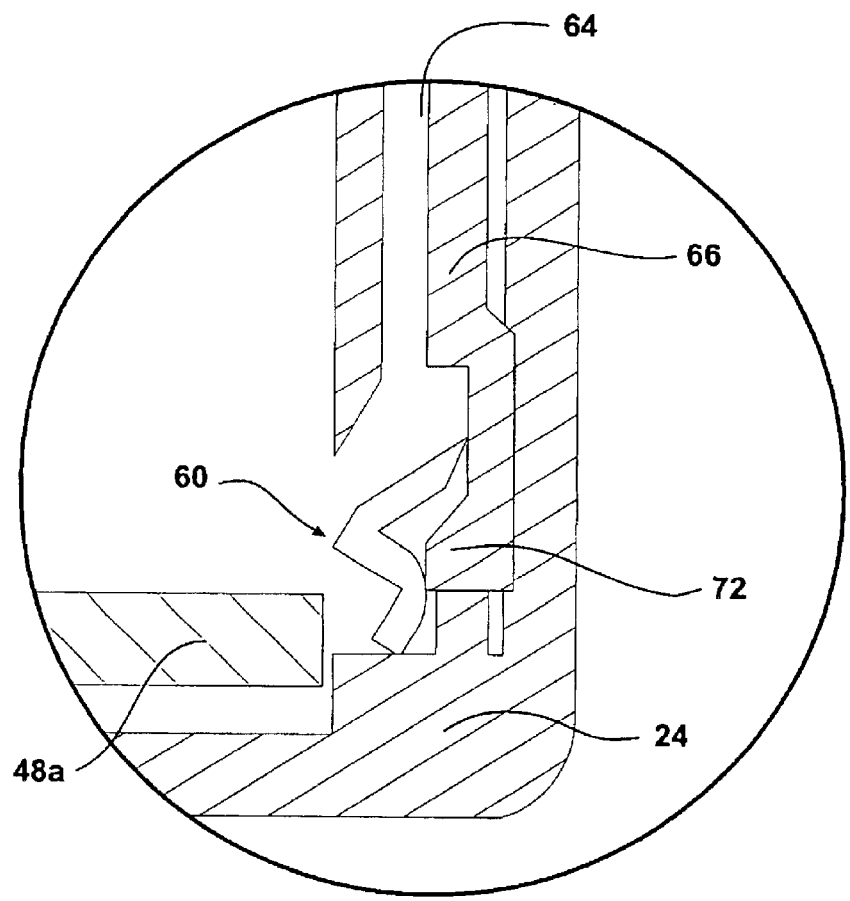
FIG. 2F is a detailed section view of the proximal portion of the hinge mechanism circled in FIG. 2C.
Figure 2G:
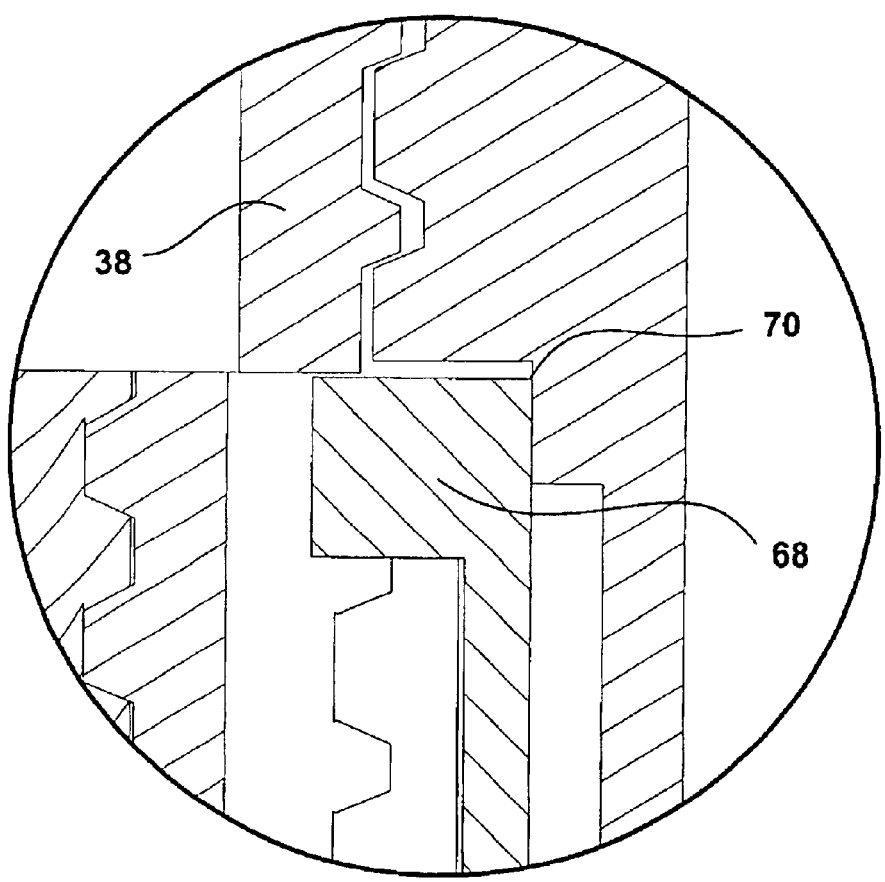
FIG. 2G is a detailed section view of the distal portion of the hinge mechanism circled in FIG. 2B.

Mechanism 10 further includes a locking mechanism which includes a plurality of biased lock hinges 60 that are coupled to a cover 62 of the rotatable outer proximal housing 24. Each of the plurality of biased lock hinges 60 are arranged at selected locations around the circumference of the cover and extend from the cover 62 in a distal direction. As shown in FIG. 2a each of the hinges 60 include a shoulder 60a and a arm 60b. The locking mechanism further includes a plurality of lock arms 64. Each of the lock arms 64 is arranged so that it is in alignment with a respective one of the lock hinges 60. Each of the lock arms 64 includes a head portion 66 and a inwardly extending foot portion 68. Initially, as shown in FIGS. 2a and 2g, the foot portion 68 of each lock arm 64 sits within a first radial shoulder 70 provided on an internal surface of the rotatable outer proximal housing 24. When in this position, an inwardly extending lip 72 of the head portion 66 is placed in abutment with the arm 60b of a corresponding lock hinge 60 as shown in FIG. 2e. Each of the lock hinges 60 is biased to move in an outward radial direction, however when the inwardly extending lip 72 of the head portion 66 is in abutment with the arm 60b of a corresponding lock hinge 60 it prevents the outward radial movement of the lock hinge 60 as shown in FIG. 2e. In addition, when the lock hinge 60 is in this position, the shoulder 60a of the lock hinge 60 is arranged in abutment with the head portion 48a of the plunger 48 to thereby prevent the distal movement of the plunger 48 (see FIG. 2e). The remaining structure and operation of the locking mechanism will be described below in the discussion of the operation of the stent delivery system in accordance with the invention.

Figures 4A, 4B, 4C, 4D:
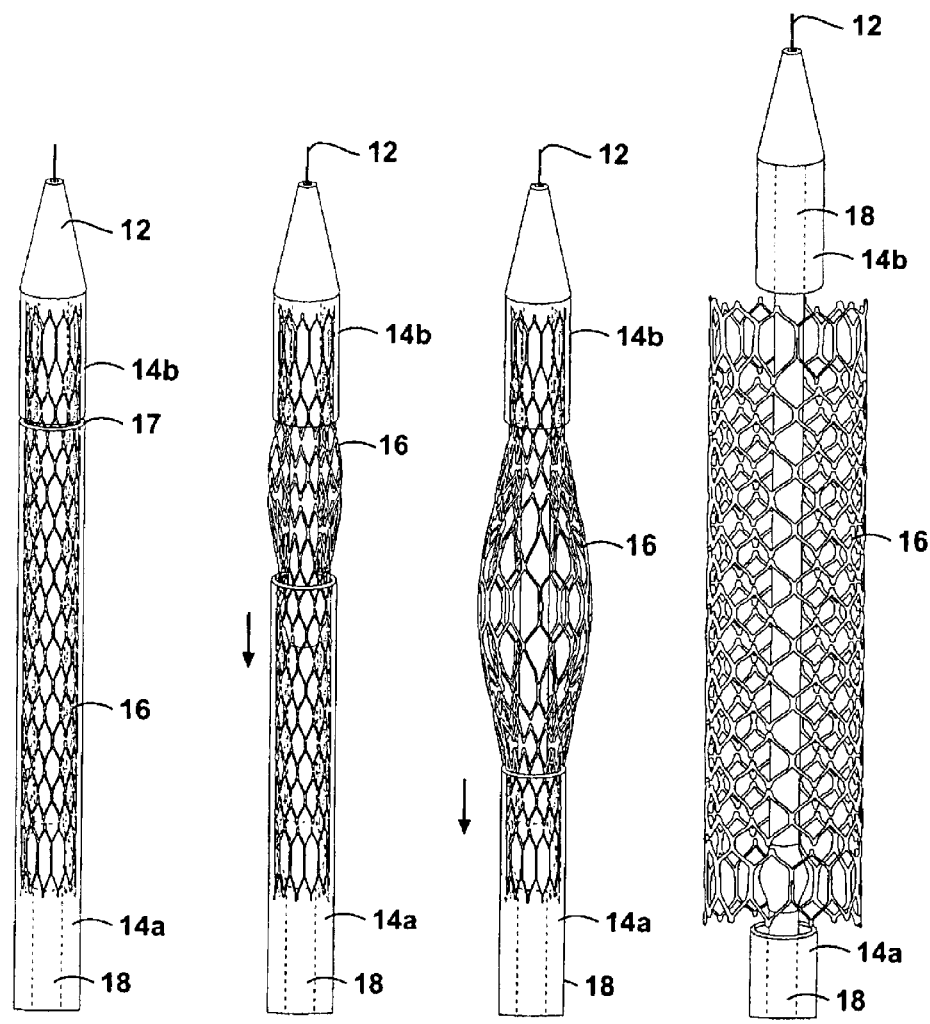
FIG. 4a-4d is a chronological series of schematic drawings showing the stent in progressive stages of deployment.

The basic operation of the stent delivery system in accordance with the invention will now be described with reference to FIGS. 2a–2d and FIGS. 4a–4d. First, the system is introduced into a vessel to be treated and then fed within the vessel over a guidewire 19 contained in a lumen in the inner tubular member 18. The tip 12 of the system is fed through the vessel until it is placed into a desired location in the vessel to be treated. Initially, as shown in FIGS. 2a and 4a, the distal end of the proximal sheath portion 14a and the proximal end of the distal sheath portion 14b are in abutment to thereby maintain the stent 16 in the compressed state. Once the preloaded stent 16, covered by the sheath 14, is positioned at the site to be treated, the physician begins rotating rotatable outer proximal housing 24 of the mechanism 10. As the rotatable outer proximal housing 24 is rotated the internal threads 28 of the housing 24, which are mated with the external threads 40 of the cup shaped insert 38, cause the cup shaped insert 38 to move in a proximal direction. Since the cup shaped insert 38 is fixedly attached to the proximal sheath portion 14a at location 46 the proximal movement of the cup shaped insert 38 causes the proximal sheath portion 14a to also move in a proximal direction as shown in FIG. 2b. This initial proximal movement of proximal sheath portion 14a begins to expose a middle region of the stent 16 as shown in FIG. 2b and FIG. 4b. During this initial proximal movement of the proximal sheath portion 14a the distal sheath portion 14b and the distal tip 15 of the system remain stationary.

As the cup shaped insert 38 is moving in a proximal direction the annular sleeve 34 is moving in a distal direction. Specifically, as the rotatable housing 24 is rotated, the throat portion 30 of the housing 24 is rotated. The internal threads 32 of the throat portion, which are mated with the external threads 36 of the annular sleeve 34, cause the annular sleeve 34 to move in a distal direction as the rotatable housing 32 is rotated. Although the annular sleeve 34 moves in an distal direction, as shown in FIG. 2b, this initial movement of annular sleeve 34 does not cause any axially movement of any other members in a system. In this regard it is noted that the plunger 48 has not moved as a result of this initial movement of annular sleeve 34 as shown in FIG. 2b. This particular arrangement, i.e. where the initial movement of the annular sleeve 34 does not result in any movement of the distal sheath portion 14b, is utilized where the junction 17 between the proximal and distal sheath portions is located towards the distal end of the stent.

If the junction 17 between the proximal and distal sheath portions 14a and 14b is located exactly over a midpoint of the stent, the mechanism 10 may be structured and arranged such that forward motion of the annular sleeve 34 will immediately initiate the forward motion of the plunger 48 and thereby cause the immediate simultaneous motion of the proximal and distal sheath portions 14a and 14b in opposite directions.

Figure 2H:
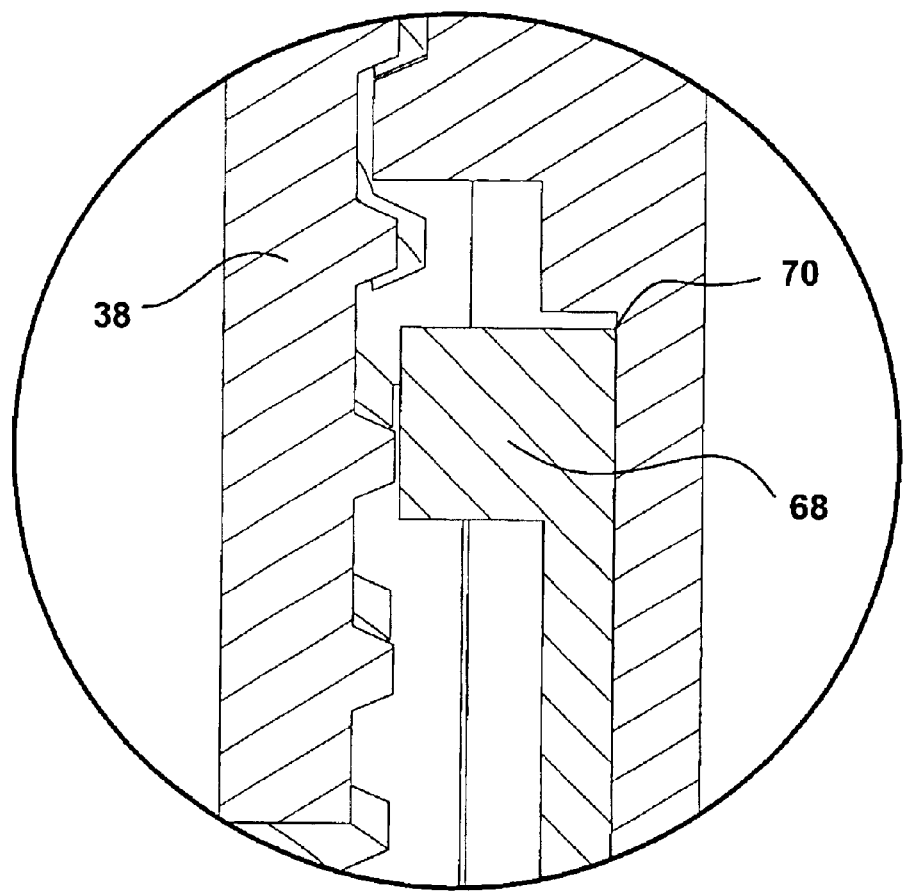
FIG. 2H is a detailed section view of the distal portion of the hinge mechanism circled in FIG. 2D.
Figure 3:
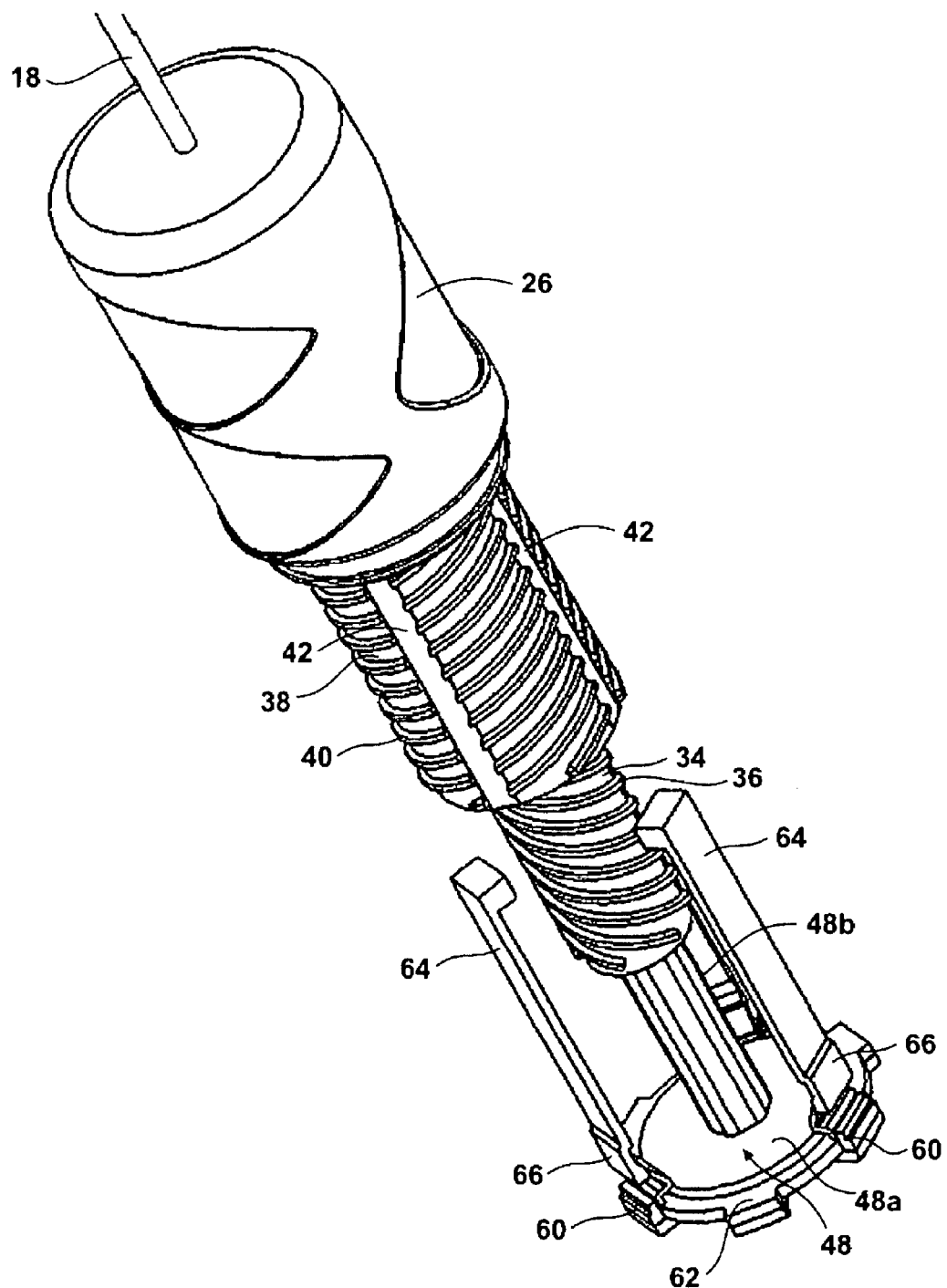
FIG. 3 is a perspective view of the deployment mechanism with the rotating handle thereof removed to reveal the inner structure of the deployment mechanism.

As the cup shaped insert 38 moves in the proximal direction eventually a leading proximal surface 74 of the cup shaped insert 38 is placed in abutment with each of the foot portions 68 of each lock arm 64 as shown in FIG. 2b. Further rotation of the rotatable housing 24 causes the leading proximal surface 74 to apply a force to each of the foot portions 68 of each lock arm 64 causing each foot portion 68 to be proximally displaced from the first radial shoulder 70 formed on the internal surface of the rotatable housing 24. As best seen in FIGS. 2g and 2h, each of the lock arms 64 are proximally displaced from the first radial shoulder 70 formed on the internal surface of the rotatable housing 24 to a second radial shoulder 76 formed on the on the internal surface of the rotatable housing 24. The state of the of lock arms 64 before and after the movement from the first radial shoulder 70 to the second radial shoulder is shown in detail in FIGS. 2g and 2h. The proximal movement of each of lock arms 64 causes the inwardly extending lip 72 of the head portion 66 of the lock arm 64 to be placed out of contact with the arm 60b of the corresponding lock hinge 72. The state of the head portion 66 of each of the lock arms 64 before and after the movement from the first radial shoulder 70 to the second radial shoulder 76 is shown in detail in FIGS. 2e and 2f. The movement of the head portion 66 of each of the lock arms 64 enables each of the lock hinges 60 to move in an radial outward direction thereby moving the shoulder 60a of each of the lock hinges 60 out of abutting contact with the head 48a of the plunger (see FIG. 2f). In this position, as shown in FIG. 2c, each of the lock arms 64 and each of the lock hinges 60 are in a clearance position relative to the head 48a of the plunger 48.

At substantially the same time that the cup shaped member 38 is displacing each of the lock arms 64 in a distal direction, the annular sleeve 34 has moved to a position where the radially inwardly extending lip 56 of annular sleeve 34 is placed in abutment with outward radially extending lip 54 of the stem portion 48b of the plunger 48. The movement of the annular sleeve 34 during this initial phase is reflected by comparing the state of the annular sleeve 34 in FIG. 5a, i.e. its starting position, and its state in FIG. 5b, i.e. a state where the radially inwardly extending lip 56 of annular sleeve 34 is placed in abutment with outward radially extending lip 54 of the stem portion 48b of the plunger 48.

In the above described manner, the plunger 48 is substantially simultaneously unlocked from the locking mechanism and operably coupled to the annular sleeve 34. At this point, further rotation of the rotatable outer proximal housing 24 causes the plunger 48 to move forward conjointly with the annular sleeve 34. The plunger 48 is coupled to the distal tip 12 of the catheter, via the inner tubular member 18, and the distal tip 12 of the catheter is coupled to the distal sheath portion 14b of the sheath 14. Thus, the distal movement of the plunger 48 causes the distal sheath portion 14b of the sheath 14 to move in a distal direction thereby further exposing the stent 16. At the same time that the distal sheath portion 14b is moving in a distal direction the proximal sheath portion 14a of the sheath 14 continues to move in a proximal direction by virtue of the continued movement of cup shaped insert 38, as shown in FIG. 4c. In this manner, upon further rotation of the rotatable outer proximal housing 24, the proximal sheath portion 14a can be moved in a proximal direction and simultaneously the distal sheath portion 14b can be moved in a distal direction until the stent 16 is fully released as shown in FIG. 2d and FIG. 4d.

The embodiment of stent delivery system of the present invention disclosed above overcomes the shortcomings in the prior art delivery systems in that it exposes a middle region of the stent before the end regions of the stent expand and are fully released, only after which the entire stent expands to its final diameter at the same time. By virtue of the deployment of the stent in this manner, stent movement during deployment of the stent is minimized thereby enabling the accurate positioning of the stent within the vessel to be treated. Further, since the middle region of the stent is exposed prior to the exposure and release of the end portions of the stent, the stent may be safely positionally adjusted within the vessel by the physician prior to final release of the stent. In prior art delivery systems, small adjustments of this type could not be safely performed since the exposed end portion of even a partially released stent could damage the vessel if the stent was moved. Finally, since middle area of the stent is exposed prior to the exposure and release of the terminal end portions of the stent, the spring effect, and jumping of the stent caused by the spring effect, is eliminated.

Although mechanism 10 described above is used to effectuate the controlled movement of the proximal sheath portion 14a in the proximal direction and the controlled movement of the distal sheath portion 14b in the distal direction, other means could be utilized to effectuate the movement of the proximal sheath portion 14a and distal sheath portion 14b. For example, separate wires could be attached to the proximal sheath portion 14a and distal sheath portion 14b, the wires being accessible to a physician at a proximal end of the system, the wires enabling the physician to manually control the movement of the proximal sheath portion 14a and distal sheath portion 14b . These and other modifications are considered within the scope of the invention and the present disclosure.

A stent delivery system according to another aspect of the invention is shown in FIGS. 6a–6d. The stent delivery system includes an outer tubular member 80, an intermediate tubular member 82 arranged within the outer tubular member 80, an inner tubular 18 member arranged within the intermediate tubular member 82 and a self-expanding stent 16 arranged between the inner tubular member 18 and the intermediate tubular member 82. The outer tubular and intermediate tubular members, 80 and 82, are movable relative to one another and extend outside the body of the person being treated and are thus manually accessible to the operator. Thus, the outer tubular member 82 and the intermediate tubular member 82 may be independently retracted in a proximal direction during stent deployment.

Figures 6A, 6B, 6C, 6D:
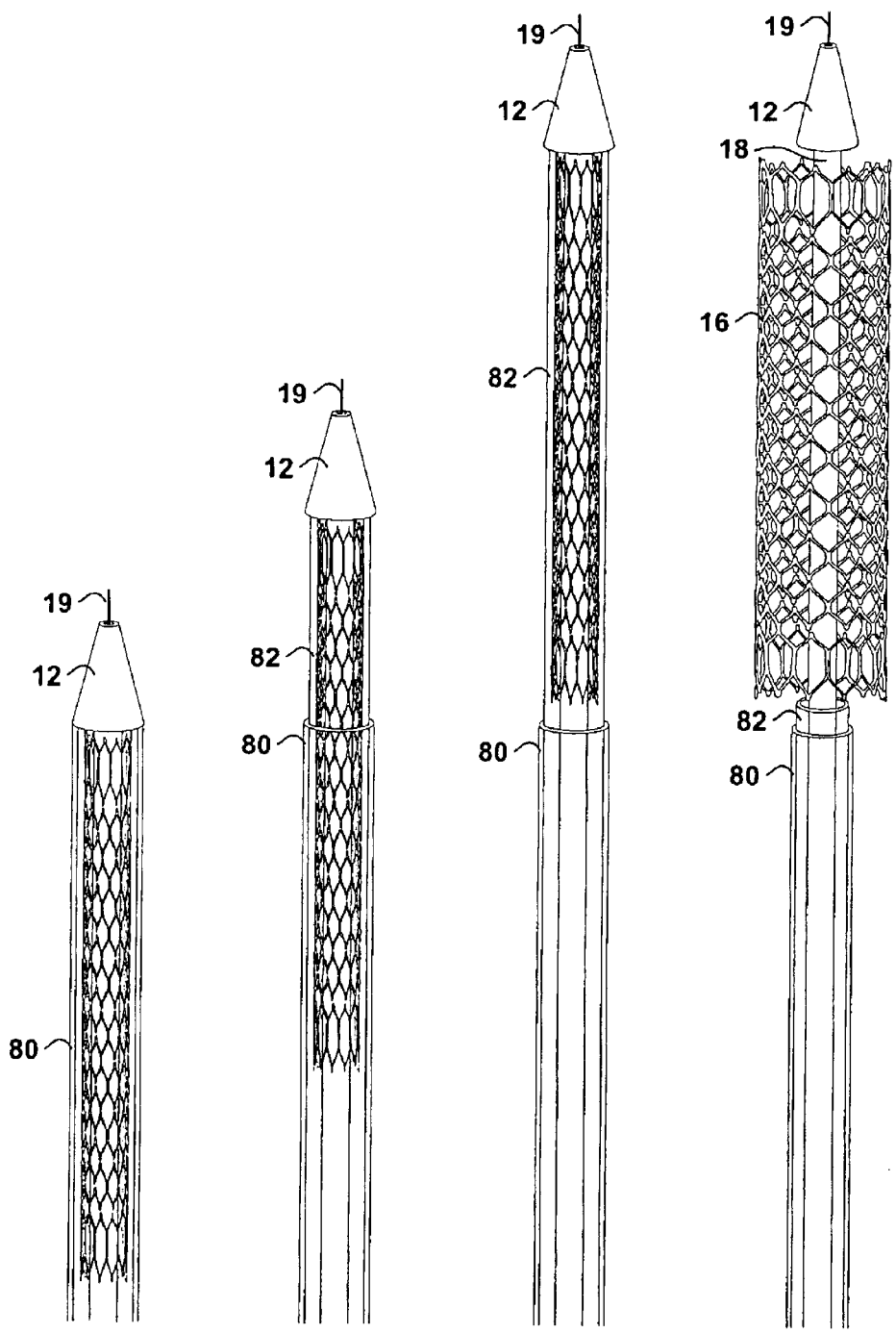
FIG. 6a-6d is a chronological series of schematic drawings showing a stent delivery system according to another aspect of the invention, the figures showing the stent in progressive stages of expansion.

The stent delivery system is first delivered to a treatment site in a conventional manner. Then the outer tubular member 80 is first retracted to a clearance position relative to the stent as shown in FIG. 6c. Thereafter, the intermediate tubular member 82 is retracted to a clearance position relative to the stent to thereby release the stent 16 as shown in FIG. 6d. Since the outer tubular member 80 is retracted first, before the retraction of the intermediate member 82 and the release of the stent 16, the effect of the "push pull" phenomenon is significantly reduced.

Figure 7A:
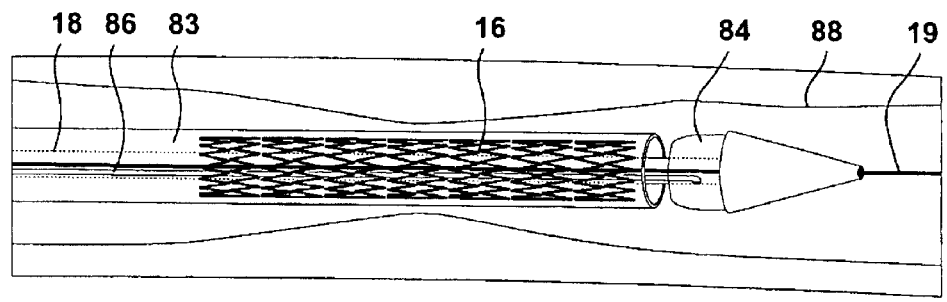
FIG. 7a-7d is a chronological series of schematic drawings showing a stent delivery system according to yet another aspect of the invention, the figures showing the stent in progressive stages of expansion.
Figure 7B:
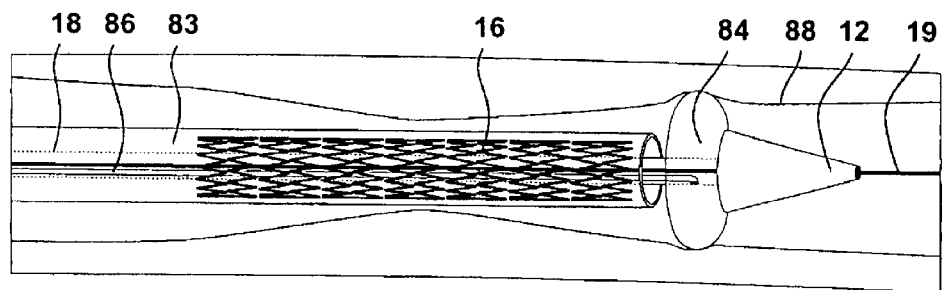
Figure 7C:
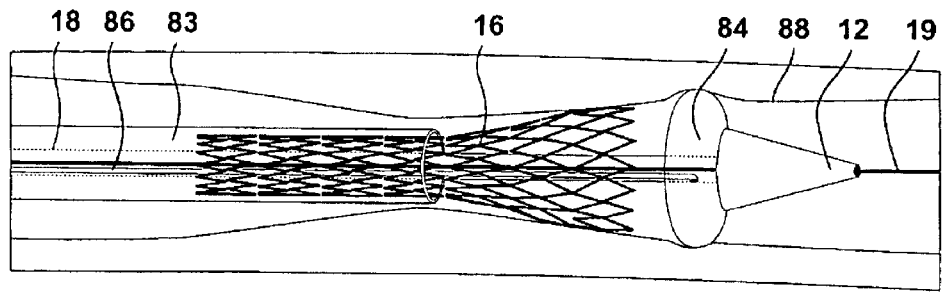
Figure 7D:
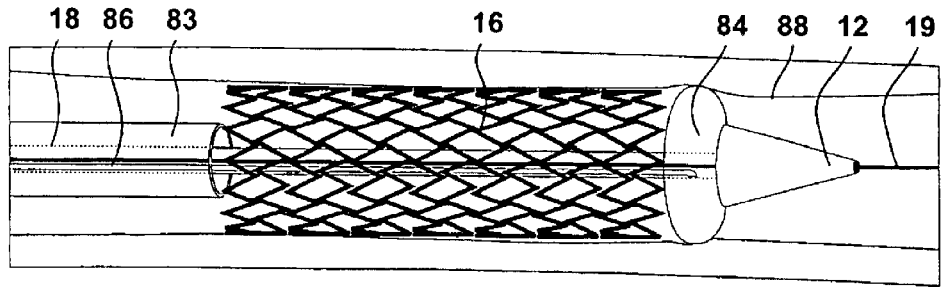

A stent delivery system according to another aspect of the invention is shown in FIGS. 7a–7d. The stent delivery system includes an outer tubular member 83, an inner tubular member 18, a stent 16 arranged between the inner tubular member 18 and the outer tubular member 83 and an inflatable balloon 84 coupled to a tip 12 of the catheter. As shown the balloon 84 is distally arranged relative to the stent 16 and a terminal end of the outer tubular member 83. The outer tubular member 83 extends outside the body of the person being treated and thus is manually accessible to the operator. The outer tubular member 83 is manually retracted back to release the stent 16. During the procedure the stent delivery system introduced to a treatment site in a conventional manner over a wire. Once the chamber with the preloaded stent and the tip 12 of the catheter are placed in the proper position the balloon 84 is inflated via a balloon lumen 86 provided within the inner tubular member 18 until the surface of the balloon 84 is placed in abutment with wall of the vessel 88 as shown in FIG. 7b. This effectively locks the system in place thereby eliminating any undesired movement of the system during stent deployment. After the balloon 84 is inflated the outer tubular member 83 is retracted to thereby release the stent 16 as shown in FIGS. 7c and 7d. Since the system is effectively locked in place by the balloon 84, movement of the system during the deployment of the stent 16 is eliminated and accurate placement of the stent is promoted. After the stent 16 has been properly deployed the balloon 84 may be deflated using the same balloon lumen 86 to thereby enable the removal of the catheter. This system is also beneficial in prevention of distal embolization effect during the manipulations with the catheter and the stent in the diseased segment of the vessel. The inflated balloon will stop all thrombotic and atherosclerotic emboli from traveling distally, which can cause blockage of the distal branches of the vessel with potential ischemia and necrosis if there were no balloon. Prior to deflation of the balloon all trapped particles can be aspirated into the sheath and the system can be safely removed.

The above disclosure is intended to be illustrative and not exhaustive. These examples and description will suggest may variations and alternatives to one of ordinary skill in the art. All these variations and alternatives are intended to be included within the scope of the attached claims. Those familiar with the may recognize other equivalents to the specific embodiment disclosed herein which equivalents are also intended to be encompassed by the claims attached hereto.

We claim:

1. A stent delivery system comprising:

a catheter system including an elongate member including a chamber arranged at a distal end of said system, said chamber being structured and arranged to receive a preloaded stent;

a sheath for covering said stent receiving section, said sheath having a proximal sheath portion extending over a proximal portion of said chamber and structured and arranged to be moveable in a proximal direction and a distal sheath portion extending over a distal portion of said chamber structured and arranged to be moveable in a distal direction; and means for controlling the movement of said proximal sheath portion in said proximal direction and means for controlling the movement of said distal sheath portion in said distal direction;

wherein said means for controlling the movement of said proximal sheath portion in said proximal direction and the movement of said distal sheath portion in said distal direction comprises:

a rotatable proximal housing; and a stationary distal housing operably coupled to said rotatable outer proximal housing;

wherein said rotatable proximal housing includes an internal throat portion; and wherein said means for controlling the movement of said proximal sheath portion in said proximal direction and the movement of said distal sheath portion in said distal direction further comprises:

an annular sleeve operably coupled to said throat portion of said rotatable proximal housing such that upon rotation of said rotatable proximal housing said annular sleeve moves in a distal direction.

2. The stent delivery system according to claim 1, further comprising:

an inner tubular member having a first and a second end, said first end of said inner tubular member operably coupled to said means for manually controlling the movement of said distal sheath portion in said distal direction, said second end of said inner tubular member operably coupled to said distal sheath portion.

3. The stent delivery system according to claim 2, wherein said proximal sheath portion is operably coupled to said means for controlling the movement of said proximal sheath portion in said proximal direction and the movement of said distal sheath portion in said distal direction.

4. The stent delivery system according to claim 3, wherein said means for controlling the movement of said proximal sheath portion in said proximal direction and the movement of said distal sheath portion in said distal direction further comprises:

a cup shaped insert operably coupled to said rotatable proximal housing such that upon rotation of said rotatable proximal housing said cup shaped insert moves in a proximal direction; and wherein said proximal sheath portion is coupled to said cup shaped insert such that upon rotation of said rotatable proximal housing said proximal sheath portion moves in a proximal direction.

5. The stent delivery system according to claim 2, wherein said inner tubular member has a guidewire lumen.

6. The stent delivery system according to claim 2, wherein said inner tubular member has a multichannel construction, one of said channels being structured and arranged to receive a guidewire and another one of said channels being structured and arranged to permit simultaneous flushing or instillation of fluid.

7. The stent delivery system according to claim 1, wherein said means for controlling the movement of said proximal sheath portion in said proximal direction and the movement of said distal sheath portion in said distal direction further comprises:
  a plunger operably coupled to an inner tubular member, said plunger being operably coupled to said annular sleeve during at least a selected phase of movement of said annular sleeve such that upon rotation of said rotatable proximal member said plunger moves conjointly with said annular sleeve in a distal direction thereby moving said distal sheath portion in said distal direction.

8. The stent delivery system according to claim 1, wherein said proximal sheath portion terminates at a distal edge and said distal sheath portion terminates at a proximal edge, said distal edge of said proximal sheath portion and said proximal edge of said distal sheath portion initially abut one other so that said sheath initially completely a stent.

9. The stent delivery system accordingly to claim 8, wherein said distal edge of said proximal sheath portion and said proximal edge of said distal sheath portion initially abut one another at a location that substantially corresponds to a midpoint of said stent.

10. A stent delivery system comprising:
  a catheter system including an elongate member including a chamber arranged at a distal end of said system, said chamber being structured and arranged to receive a preloaded stent;
  a sheath for covering said stent receiving section, said sheath having a proximal sheath portion extending over a proximal portion of said chamber and structured and arranged to be moveable in a proximal direction and a distal sheath portion extending over a distal portion of said chamber structured and arranged to be moveable in a distal direction; and
  means for controlling the movement of said proximal sheath portion in said proximal direction and means for controlling the movement of said distal sheath portion in said distal direction;
  wherein said means for controlling the movement of said proximal sheath portion in said proximal direction and the movement of said distal sheath portion in said distal direction further comprises:
  a plunger operably coupled to an inner tubular member, said plunger being operably coupled to an annular sleeve during at least a selected phase of movement of said annular sleeve such that upon rotation of said rotatable proximal member said plunger moves conjointly with said annular sleeve in a distal direction thereby moving said distal sheath portion in said distal direction; and
  wherein said means for controlling the movement of said proximal sheath portion in said proximal direction and the movement of said distal sheath portion in said distal direction further comprises:
  a locking mechanism, said locking mechanism being structured and arranged to prevent the distal movement of said plunger during an initial phase of movement of said annular sleeve and permit said plunger to move conjointly with said annular sleeve during said selected phase of movement of said annular sleeve in the system, when the junction of said distal and proximal sheath portions are located initially towards a distal end of said stent receiving section.

11. The stent delivery system according to claim 10, wherein said locking mechanism comprises:
  at least one lock arm having a foot portion and a head portion;
  and at least one lock hinge having a shoulder portion and a arm portion;
  wherein said shoulder portion of said lock hinge is arranged in abutting contact with a head of said plunger to thereby prevent the distal movement of said plunger during said initial phase of movement of said annular sleeve;
  wherein said lock hinge is biased to move to a clearance position relative to said head of said plunger and said head portion of said lock arm is placed in abutting contact with said arm portion of said lock hinge during said initial phase of movement of said annular sleeve to thereby prevent said lock hinge from moving to said clearance position thereby maintaining said shoulder portion of said lock hinge in abutment with said head of said plunger.

12. The stent delivery system according to claim 11, wherein a cup shaped insert has a leading proximal surface that is placed into contact with said foot portion of said at least one lock arm when said cup shaped portion moves in said proximal direction, said proximal surface being placed into contact with said foot portion at substantially the same time as a commencement of said selected phase of movement of said annular sleeve, said proximal surface of said cup shaped insert applying a force to said foot portion of said at least one arm to thereby move said lock are in a proximal direction thereby moving said head of said lock arm out of abutting contact with said abutting contact with said arm portion of said lock hinge permitting said lock hinge to move to clearance position thereby permitting said plunger to move in a distal direction.

13. The stent delivery system according to claim 12, wherein said plunger includes a stem portion that extends distally from said head of said plunger, said stem portion structured and arranged so that it extends into an axial bore of said annular sleeve, said stem portion having an outer surface and a radially outwardly extending lip that extends outwardly from said outer surface, and
  wherein said annular sleeve has an inner surface and a radially inwardly extending lip, and
  wherein at said commencement of said selected phase of movement of said annular sleeve said radially outwardly extending lip of said stem portion is placed in abutment with said radially inwardly extending lip of said annular sleeve such that further movement of said annular sleeve in said distal direction causes said plunger to move in said distal direction.

14. The stent delivery system according to claim 13, wherein said cup shaped insert has an external surface provided with at least one recessed axial channel and an internal surface of said stationary distal housing is provided with at least one key structured and arranged to mate with said at least one recessed axial channel, said at least one recessed axial channel and said at least one key cooperating to permit an axial movement of said cup shaped insert while at the same time preventing a rotational movement of said cup shaped insert.

15. A stent delivery system comprising:
  a catheter system including an elongate member including a chamber arranged at a distal end of said system, said chamber being structured and arranged to receive a preloaded stent;

a sheath for covering said stent receiving section, said sheath having a proximal sheath portion extending over a proximal portion of said chamber and structured and arranged to be moveable in a proximal direction and a distal sheath portion extending over a distal portion of said chamber structured and arranged to be moveable in a distal direction; and means for controlling the movement of said proximal sheath portion in said proximal direction and means for controlling the movement of said distal sheath portion in said distal direction;

wherein said means for controlling the movement of said proximal sheath portion in said proximal direction and the movement of said distal sheath portion in said distal direction comprises:

a rotatable proximal housing; and a stationary distal housing operably coupled to said rotatable outer proximal housing;

wherein said rotatable proximal housing includes an internal throat portion; and wherein said means for controlling the movement of said proximal sheath portion in said proximal direction and the movement of said distal sheath portion in said distal direction further comprises:

an annular sleeve operably coupled to said throat portion of said rotatable proximal housing such that upon rotation of said rotatable proximal housing said annular sleeve moves in a distal direction wherein said means for controlling the movement of said proximal sheath portion in said proximal direction and the movement of said distal sheath portion in said distal direction further comprises:

a plunger operably coupled to an inner tubular member, said plunger being operably coupled to said annular sleeve during at least a selected phase of movement of said annular sleeve such that upon rotation of said rotatable proximal member said plunger moves conjointly with said annular sleeve in a distal direction thereby moving said distal sheath portion in said distal direction; and wherein said means for controlling the movement of said proximal sheath portion in said proximal direction and the movement of said distal sheath portion in said distal direction further comprises:

means for operably coupling said plunger to said annular sleeve such that as soon as said annular sleeve begins moving in a distal direction said plunger and said distal portion of said sheath also move conjointly with said sleeve in said distal direction when a junction between said proximal and distal sheath portions is initially arranged over a middle portion of said stent receiving section.

16. A stent delivery system comprising:

a sheath for covering a stent, said sheath having a proximal sheath portion structured and arranged to be moveable in a proximal direction and a distal sheath portion structured and arranged to be moveable in a distal direction;

means for controlling the movement of said proximal sheath portion in said proximal direction and means for controlling the movement of said distal sheath portion in said distal direction;

wherein said means for controlling the movement of said proximal sheath portion in said proximal direction and the movement of said distal sheath portion in said distal direction comprises:

a rotatable proximal housing; and a stationary distal housing operably coupled to said rotatable outer proximal housing;

wherein said rotatable proximal housing includes an internal throat portion; and wherein said means for controlling the movement of said proximal sheath portion in said proximal direction and the movement of said distal sheath portion in said distal direction further comprises:

an annular sleeve operably coupled to said throat portion of said rotatable proximal housing such that upon rotation of said rotatable proximal housing said annular sleeve moves in a distal direction; and whereby when said proximal sheath portion is moved in said proximal direction and said distal sheath portion is moved in said distal direction a middle portion of said stent is exposed prior to the exposure and expansion of the terminal end portions of said stein.

17. The stent delivery system according to claim 16, further comprising means for controlling the movement of said proximal sheath portion in said proximal direction and the movement of said distal sheath portion in said distal direction, said means comprising:

at least a first member moveable in a proximal direction, said first member operably coupled to said proximal sheath portion; and at least a second member movable in a distal direction, said second member operably coupled to said distal sheath portion.

18. The stent delivery system according to claim 17, wherein said means for controlling the movement of said proximal sheath portion in said proximal direction and the movement of said distal sheath portion in said distal direction is manually operable by an operator.

19. A catheter assembly for delivering and deploying a self-expanding stent, comprising:

an elongate member having an axially extending stent-mounting portion at a distal end region thereof;

a self-expanding stent having proximal and distal ends coaxially mounted in a collapsed configuration on said stent-mounting portion of said elongate member;

an outer tubular proximal sheath portion coaxially mounted on said elongate member at said distal region thereof, said proximal sheath portion having a distal end and being structured and arranged to move between a closed position in which said distal end of said proximal sheath portion overlies said stent and is situated between the ends of said stent, and an open position in which said distal end of said proximal sheath portion, does not overlie said stent and is situated proximally of said proximal end of said stent;

an outer tubular distal sheath portion coaxially mounted on said elongate member at said distal region thereof, said distal sheath portion having a proximal end and being structured and arranged to move between a closed position in which said proximal end of said distal sheath portion overlies said stent and is situated between the ends of said stent, and an open position in which said proximal end of said distal sheath portion does not overlie said stent and is situated distally of said distal end of said stent;

means for controlling the movement of said proximal sheath portion situated in part at, and operable from, a proximal end region of said catheter assembly for controlling the movement of said proximal sheath portion in said proximal direction and distal sheath portions in said distal direction from said closed to said open positions thereof wherein said means for controlling the movement comprises:

a rotatable proximal housing; and a stationary distal housing operably coupled to said rotatable outer proximal housing;

wherein said rotatable proximal housing includes an internal throat portion; and wherein said means for controlling the movement of said proximal sheath portion in said proximal direction and the movement of said distal sheath portion in said distal direction further comprises:

an annular sleeve operably coupled to said throat portion of said rotatable proximal housing such that upon rotation of said rotatable proximal housing said annular sleeve moves in a distal direction; and whereby said stent is delivered to a desired treatment site within said vessel while mounted in a collapsed configuration on said stent-mounting portion of said elongate member with said proximal and distal sheath portions situated in their closed positions restraining the expansion of said stent, and is deployed at said treatment site by operation of said means for controlling to move said proximal and distal sheath portions to their open positions to allow the expansion and deployment of said stent.

20. The catheter assembly for delivering and deploying a self-expanding stent according to claim 19, wherein when in their closed positions said proximal end of said distal sheath portion and said distal end of said proximal sheath portion are in mutual engagement.

21. The catheter assembly for delivering and deploying a self-expanding stent according to claim 19, wherein when in their closed positions, the proximal and distal sheath portions overlie the entire stent.

22. The catheter assembly for delivering and deploying a self-expanding stent according to claim 19, wherein said control mechanism includes means for moving said proximal and distal sheath portions from there closed positions to their open positions in a coordinated manner.

23. The catheter assembly for delivering and deploying a self-expanding stent according to claim 19, wherein said proximal and distal sheath portions comprise separate and distinct members.

24. An elongate catheter assembly for delivering and deploying a self-expanding stent, comprising:

an elongate member having an axially extending stent-mounting portion at a distal end region thereof;

an outer tubular proximal sheath portion coaxially mounted on said elongate member at said distal region thereof, said proximal sheath portion being structured and to move between a closed position in which said proximal sheath portion partially overlies said stent-mounting portion of said elongate member, and an open position in which said proximal sheath portion does not overlie said stent-mounting portion of said elongate member or any part thereof;

an outer tubular distal sheath portion coaxially mounted on said elongate member at said distal region thereof, said distal sheath portion being structured and arranged to move between a closed position in which said distal sheath portion partially overlies said stent-mounting portion of said elongate member, and an open position in which said distal sheath portion does not overlie said stent-mounting portion or any part thereof;

a means for controlling the movement situated in part at, and operable from, a proximal end region of said catheter assembly for controlling the movement of said proximal and distal sheath portions from said closed to said open positions thereof;

wherein said means for controlling the movement comprises:

a rotatable proximal housing; and a stationary distal housing operably coupled to said rotatable outer proximal housing;

wherein said rotatable proximal housing includes an internal throat portion; and wherein said means for controlling the movement further comprises:

an annular sleeve operably coupled to said throat portion of said rotatable proximal housing such that upon rotation of said rotatable proximal housing said annular sleeve moves in a distal direction; and whereby a stent is delivered to a desired treatment site within said vessel while mounted in a collapsed configuration on said stent-mounting portion of said elongate member with said proximal and distal sheath portions situated in their closed positions restraining the expansion of the stent, and is deployed at said treatment site by operation of said means for controlling to move said proximal and distal sheath portions to their open positions to allow the expansion and deployment of the stent.

25. The catheter assembly for delivering and deploying a self-expanding stent according to claim 24, wherein when in their closed positions said proximal end of said distal sheath portion and said distal end of said proximal sheath portion are in mutual engagement.

26. The catheter assembly for delivering and deploying a self-expanding stent according to claim 24, wherein when in their closed positions, the proximal and distal sheath portions overlie the entire stent.

27. The catheter assembly for delivering and deploying a self-expanding stent according to claim 24, wherein said control mechanism includes means for moving said proximal and distal sheath portions from there closed positions to their open positions in a coordinated manner.

28. The catheter assembly for delivering and deploying a self-expanding stent according to claim 24, wherein said control mechanism includes means for moving one of said proximal and distal sheath portions without moving the other of said proximal and distal sheath portions.

29. The catheter assembly for delivering and deploying a self-expanding stent according to claim 24, wherein said proximal and distal sheath portions comprise separate and distinct members.

* * * * *